(12) United States Patent
Zhao et al.

(10) Patent No.: US 8,030,560 B2
(45) Date of Patent: *Oct. 4, 2011

(54) HIGHLY TRANSFORMABLE ELITE DOUBLED HAPLOID LINE PHWVZ

(75) Inventors: Zuo-Yu Zhao, Johnston, IA (US); Ning Wang, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/509,538

(22) Filed: Jul. 27, 2009

(65) Prior Publication Data

US 2009/0288217 A1   Nov. 19, 2009

Related U.S. Application Data

(63) Continuation of application No. 11/755,083, filed on May 30, 2007, now abandoned.

(51) Int. Cl.
*A01H 5/00* (2006.01)
*A01H 5/10* (2006.01)
*A01H 1/02* (2006.01)
*C12N 5/04* (2006.01)

(52) U.S. Cl. .......... 800/320.1; 800/275; 800/300.1; 800/303; 800/288; 435/412; 435/421; 435/462; 435/468

(58) Field of Classification Search .......... None
See application file for complete search history.

(56) References Cited

U.S. PATENT DOCUMENTS

| | | | | |
|---|---|---|---|---|
| 5,859,354 | A * | 1/1999 | Williams | 800/320.1 |
| 7,022,894 | B2 * | 4/2006 | Ranch et al. | 800/268 |
| 2008/0072343 | A1 * | 3/2008 | Wang et al. | 800/278 |
| 2008/0072344 | A1 * | 3/2008 | Wang et al. | 800/278 |
| 2008/0108072 | A1 * | 5/2008 | Chicoine et al. | 435/6 |
| 2009/0293141 | A1 | 11/2009 | Wang et al. | |
| 2009/0300789 | A1 | 12/2009 | Wang et al. | |
| 2010/0017908 | A1 | 1/2010 | Zhao et al. | |

* cited by examiner

*Primary Examiner* — David T Fox

(57) ABSTRACT

A novel double haploid maize line designated PHWVZ and seed, plants and plant parts thereof. Methods for producing a maize plant that comprise crossing double haploid maize line PHWVZ with another maize plant. Methods for producing a maize plant containing in its genetic material one or more traits introgressed into PHWVZ through backcross conversion and/or transformation, and to the maize seed, plant and plant part produced thereby. Hybrid maize seed, plant or plant part produced by crossing the double haploid line PHWVZ or a trait conversion of PHWVZ with another maize line. Inbred maize lines derived from double haploid maize line PHWVZ, methods for producing other inbred maize lines derived from double haploid maize line PHWVZ and the inbred maize lines and their parts derived by the use of those method.

19 Claims, No Drawings

HIGHLY TRANSFORMABLE ELITE DOUBLED HAPLOID LINE PHWVZ

CROSS-REFERENCE TO RELATED APPLICATIONS

This application is a continuation of U.S. patent application Ser. No. 11/755,083 filed on May 30, 2007, now abandoned, the content of which is hereby incorporated by reference in its entirety.

FIELD OF THE INVENTION

The present invention relates to the field of plant breeding and maize transformation.

BACKGROUND OF THE INVENTION

Transformation of elite maize inbreds is an important technology for developing maize inbreds and hybrids with improved agronomic traits. Work by Armstrong and others (D. D. Songstad, W. L. Petersen, C. L. Armstrong, American Journal of Botany, Vol. 79, pp. 761-764, 1992) showed that it was possible to interbreed a more culturable, agronomically poor maize line (A188) with an agronomically desirable, less transformable line (B73) to produce a novel line, Hi-II, with increased culturability and regeneration. Hi-II maize has been used for maize transformation for a number of years because of its high transformability and good culturability, but Hi-II is a hybrid. Non-homozygous plants used in developing transgenic traits are problematic. It is easier to determine the effects of a transgene when a uniform, homozygous, background is used in transgene development. Another disadvantage of using Hi-II in transformation is that it does not have the quality genetics that are present in current elite inbreds. When developing a transgenic product the transgene is moved into an elite background through cross pollination. After the initial cross, backcrossing is used to remove as much of the Hi-II deleterious genome as possible. This is a labor intensive and time consuming process. It would therefore be beneficial to have a homozygous maize variety that has an elite genotype while also maintaining high transformability and good response in culture.

SUMMARY OF THE INVENTION

According to the invention, there is provided a novel double haploid maize line designated PHWVZ and processes for making PHWVZ. This invention relates to seed of the doubled haploid maize line PHWVZ, to the plants of doubled haploid maize line PHWVZ, to plant parts of doubled haploid maize line PHWVZ, and to processes for making a maize plant that comprise crossing doubled haploid maize line PHWVZ with another maize plant. PHWVZ is also considered and referred to as an inbred maize line. This invention also relates to processes for making a maize plant containing in its genetic material one or more traits introgressed into PHWVZ through backcross conversion and/or transformation, and to the maize seed, plant and plant part produced by such introgression. This invention further relates to a hybrid maize seed, plant or plant part produced by crossing the doubled haploid maize line PHWVZ or an introgressed trait conversion of PHWVZ with another maize line. This invention also relates to inbred maize lines derived from doubled haploid maize line PHWVZ, to processes for making other inbred and doubled haploid maize lines derived from PHWVZ, and to the inbred maize lines and their parts derived by the use of those processes.

DEFINITIONS

ALLELE. Any of one or more alternative forms of a genetic sequence. Typically, in a diploid cell or organism, the two alleles of a given sequence typically occupy corresponding loci on a pair of homologous chromosomes.

BACKCROSSING. Process in which a breeder crosses a hybrid progeny line back to one of the parental genotypes one or more times.

BREEDING. The genetic manipulation of living organisms.

BREEDING CROSS. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed. For clarification, such new inbred varieties would be within a pedigree distance of one breeding cross of plants A and B. The process described above would be referred to as one breeding cycle.

CROSS POLLINATION. A plant is cross pollinated if the pollen comes from a flower on a different plant from a different family or line. Cross pollination excludes sib and self pollination.

CROSS. As used herein, the term "cross" or "crossing" can refer to a simple X by Y cross, or the process of backcrossing, depending on the context.

ELITE INBRED. An inbred that contributed desirable qualities when used to produce commercial hybrids. An elite inbred may also be used in further breeding for the purpose of developing further improved varieties.

INBRED. A line developed through inbreeding or doubled haploidy that preferably comprises homozygous alleles at about 95% or more of its loci.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

LOCUS. A defined segment of DNA.

NEI DISTANCE. A quantitative measure of percent similarity between two lines. Nei's distance between lines A and B can be defined as 1-(2*number alleles in common/(number alleles in A+number alleles in B). For example, if lines A and B are the same for 95 out of 100 alleles, the Nei distance would be 0.05. If lines A and B are the same for 98 out of 100 alleles, the Nei distance would be 0.02. Free software for calculating Nei distance is available on the internet at multiple locations such as, for example, at: evolution.genetics.washington.edu/phylip.html. See Nei, Proc Natl Acad Sci, 76:5269-5273 (1979) which is incorporated by reference for this purpose.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two inbred lines. Each inbred plant will have the same allele (and therefore be homozygous) at almost all of their loci. Percent identity is determined by comparing a statistically significant number of the homozygous alleles of two inbred lines. For example, a percent identity of 90% between inbred PHWVZ and other inbred line means that the two inbred lines have the same allele at 90% of their loci.

PERCENT SIMILARITY. Percent similarity as used herein refers to the comparison of the homozygous alleles of an inbred line with another plant. The homozygous alleles of PHWVZ are compared with the alleles of a non-inbred plant, such as a hybrid, and if the allele of the inbred matches at least one of the alleles from the hybrid then they are scored as similar. Percent similarity is determined by comparing a statistically significant number of loci and recording the number of loci with similar alleles as a percentage. For example, a percent similarity of 90% between inbred PHWVZ and a hybrid maize plant means that the inbred line matches at least one of the hybrid alleles at 90% of the loci. In the case of a hybrid produced from PHWVZ as the male or female parent, such hybrid will comprise two sets of alleles, one set of which will comprise the same alleles as the homozygous alleles of inbred line PHWVZ.

PLANT. As used herein, the term "plant" includes reference to an immature or mature whole plant, including a plant that has been detasseled or from which seed or grain has been removed. Seed or embryo that will produce the plant is also considered to be the plant.

SELF POLLINATION. A plant is self-pollinated if pollen from one flower is transferred to the same or another flower of the same plant.

SIB POLLINATION. A plant is sib-pollinated when individuals within the same family or line are used for pollination.

SINGLE LOCUS CONVERSION TRAIT. A trait that can be introgressed into a corn line through introgression and/or transformation of a single locus. Examples of such single locus traits include mutant genes, transgenes and native traits finely mapped to a single locus. One or more single locus conversion traits may be introduced into a single corn line.

DETAILED DESCRIPTION OF THE INVENTION AND FURTHER EMBODIMENTS

Morphological and Physiological Characteristics of PHWVZ

Doubled haploid maize line PHWVZ, can be reproduced by planting seeds of the line, growing the resulting maize plants under self-pollinating or sib-pollinating conditions with adequate isolation, and harvesting the resulting seed using techniques familiar to the agricultural arts.

Development of PHWVZ

The development of PHWVZ was initiated by crossing a Hi-II maize line with PH09B. PH09B is an elite maize line described in U.S. Pat. No. 5,859,354 and having seed deposited with the ATCC and having the deposit number: 203085. The F1 embryos produced from this cross were cultured on medium. Embryos with good type II callus and fast callus growing response were selected and plants were regenerated from the selected callus lines. The regenerated plants were grown and backcrossed with PH09B to produce BC1 embryos. These BC1 immature embryos were isolated and placed on culture medium for selection of the best type II callus and fastest growing callus. Plants were regenerated from the selected callus cultures. When the plants flowered they were self pollinated forming BC1S1 seed. The BC1S1 seeds were planted in the field. Plants were selected that were morphologically close to inbred PH09B. These selected plants were self-pollinated to produce BC1S2 immature embryos. The BC1S2 through BC1S5 embryos were screened for the following characters: 1) ability to receive T-DNA from *Agrobacterium* infection, 2) ability to initiate callus response following *Agrobacterium* infection, 3) ability to produce fast-growing and friable type II callus, 4) ability of callus tissue to be maintained on culture medium for at least 3 months, 5) ability of callus tissues to regenerate fertile plants and 6) ability of the regenerated plants to produce viable seed and good seed set. The immature embryos in these 4 generations were infected with *Agrobacterium* LBA4404 comprising a visible marker, such as CRC or GFP. After infection with the *Agrobacterium* the embryos were cultured on callus induction medium without selection pressure and evaluated at 7 days for transient expression of the visible marker. Since there was no selection pressure in the medium, both transformed and non-transformed cells could initiate callus response and the visible marker expressed only in the transformed cells and callus, but did not express in the non-transformed cells and callus. Embryos with the best transient expression and best callus response were selected and the parts of the callus tissues that did not express the visible marker on these selected embryos were used to regenerate into plants. The regenerated plants were evaluated for their fertility and seed set, as well as plant morphology close to PH09B in each generation. The selected plants were self pollinated to produce immature embryos and seeds for the next generation.

At BC1S6 generation, the selected plants were pollinated with a haploid inducer, RWS, in order to generate haploid embryos. These haploid embryos were then used to develop double haploid plants. These doubled haploid plants were fully evaluated for transformability including stable transformation frequency at callus stage, regeneration frequency of the transformed calli and the fertility and seed set of the transformed plants. Through these thorough evaluations, one doubled haploid plant was then designated to form the PHWVZ doubled haploid maize line.

Culture and Transformation Characteristics of PHWVZ

Immature embryos isolated from PHWVZ plants produce high quality of Type II callus. Three criteria were used to measure the quality of the callus tissue: callus initiation frequency, callus growth rate, and regeneration capability. The callus initiation frequency of PHWVZ is about 80% or higher. The callus tissues produced from PHWVZ embryos grow very fast (faster than Hi-II) (Table 1) and callus tissues are very friable and highly embryogenic. In contrast, immature embryos from PH09B did not produce Type II callus. Embryos from PH09B produced compact Type I callus at a low frequency, less than 3%. This compact Type I callus grows much slower than Type II callus.

TABLE 1

Comparison of Callus Growth Rate of PHWVZ and Hi-II

| Line Name | Embryo | Initial Weight (gm) | Weight at 4-Week Culture (gm) | Callus Growth Rate (times) |
|---|---|---|---|---|
| PHWVZ | 1 | 0.21 | 4.83 | 23.0 X |
| | 2 | 0.16 | 5.25 | 32.9 X |
| | 3 | 0.27 | 6.64 | 24.6 X |
| | 4 | 0.19 | 6.75 | 35.5 X |
| | 5 | 0.22 | 8.88 | 40.4 X |
| | 6 | 0.20 | 7.26 | 36.3 X |
| | Average | 0.21 | 6.60 | 31.4 X |
| Hi-II | 1 | 0.50 | 10.67 | 20.3 X |
| | 2 | 0.44 | 11.77 | 25.8 X |
| | 3 | 0.48 | 13.05 | 26.2 X |

TABLE 1-continued

Comparison of Callus Growth Rate of PHWVZ and Hi-II

| Line Name | Embryo | Initial Weight (gm) | Weight at 4-Week Culture (gm) | Callus Growth Rate (times) |
|---|---|---|---|---|
| | 4 | 0.40 | 10.40 | 25.0 X |
| | 5 | 0.32 | 9.97 | 30.2 X |
| | Average | 0.43 | 11.17 | 25.0 X |

The data presented in Table 1 demonstrated the callus growth rates of PHWVZ and Hi-II. For 4-week cultures, callus weight of PHWVZ increased 31.4 times comparing to the callus weight of initial cultures while callus weight of Hi-II increase 25 times. The callus growth rate was evaluated after callus was on maintenance medium for 4 weeks at 28C in the dark. The callus growth rate was calculated as: Callus growth rate=(callus weight at 4-week−callus weight at initial culture)/callus weight at initial culture.

The immature embryos isolated from PHWVZ plants were used for *Agrobacterium*-mediated transformation. Two selection marker genes, bar and GAT, were used to select stable transformation. The data listed in Table 2 showed that the overall transformation frequencies were % with bar selection (glufosonate tolerance) and 53.9% with GAT selection (glyphosate tolerance).

As the controls, the transformation frequency of PH09B with *Agrobacterium* was zero percent and the transformation frequency of Hi-IIxPH09B is less than 0.3%.

TABLE 2

Stable Transformation Experiments with PHWVZ

| Selection Marker | Total Embryos Infected | Stable Callus Events (%) | Regeneration (%) | Overall Frequency |
|---|---|---|---|---|
| Bar | 8,675 | 3,817 (44%) | 82% | 36.0% |
| GAT | 561 | 250 (44.6%) | 77% | 34.3% |

Morphological Characteristics of PHWVZ

PHWVZ has been characterized agronomically both in the field and in the greenhouse. When grown in the field at Johnston, Iowa it reached 50% pollen shed and 50% silk at 1580 Growing Degree Units (GDU) and 1630 GDU respectively. PHWVZ had an average plant height of 213 cm and average ear height of 82 cm. PHWVZ has yellow dent kernels and purple cob and produced about 183 seeds/ear on average. When it was grown in greenhouse conditions, PHWVZ averaged 259 cm in height and produced about 288 kernels/ear. In the greenhouse PHWVZ averaged about 69 days from planting to flowering and about 100 days from planting to harvest.

Genotypic Characteristics of PHWVZ

Molecular markers have been used to analyse the genetic make-up of PHWVZ. The 303 molecular markers in Table 3 were polymorphic between PH09B and Hi-II and were used for analysis. By extrapollating the % of markers from each parent into the percentage of heredity, one can estimate that about 38.5% of the gemone was derived from Hi-II and about 61.5% was derived from PH09B. The marker data indicated the origins (either from PH09B or Hi-II) of different proportions of the chromosomal regions on each of the 10 maize chromosomes.

A plant can be identified by its genotype. The genotype of a plant can be characterized through a genetic marker profile, which can identify plants of the same variety or a related variety, or be used to determine or validate a pedigree. The SSR profile of Inbred PHWVZ can be found in Table 3.

As a result of the doubled haploid process, PHWVZ is substantially homozygous. This homozygosity has been characterized at the loci shown in the marker profile provided herein. An F1 hybrid made with PHWVZ would comprise the marker profile of PHWVZ shown herein. This is because an F1 hybrid is the sum of its inbred parents, e.g., if one inbred parent is homozygous for allele x at a particular locus, and the other inbred parent is homozygous for allele y at that locus, the F1 hybrid will be x.y (heterozygous) at that locus. The profile can therefore be used to identify hybrids comprising PHWVZ as a parent, since such hybrids will comprise two sets of alleles, one set of which will be from PHWVZ. The determination of the male set of alleles and the female set of alleles may be made by profiling the hybrid and the pericarp of the hybrid seed, which is composed of maternal parent cells. One way to obtain the paternal parent profile is to subtract the pericarp profile from the hybrid profile.

Subsequent generations of progeny produced by selection and breeding are expected to be of genotype x (homozygous), y (homozygous), or x.y (heterozygous) for these locus positions. When the F1 plant is used to produce an inbred, the resulting inbred should be either x or y for that allele. In that regard, a unique allele or combination of alleles unique to that inbred can be used to identify progeny plants that retain those unique alleles or combinations of alleles.

Therefore, in accordance with the above, an embodiment of this invention is a PHWVZ progeny maize plant or plant part that is a first generation (F1) hybrid maize plant comprising two sets of alleles, wherein one set of the alleles is the same as PHWVZ at all of the SSR loci listed in Table 3. A maize cell wherein one set of the alleles is the same as PHWVZ at all of the SSR loci listed in Table 3 is also an embodiment of the invention. This maize cell may be a part of a hybrid seed, plant or plant part produced by crossing PHWVZ with another inbred maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don et al., "Assessing Probability of Ancestry Using Simple Sequence Repeat Profiles: Applications to Maize Hybrids and Inbreds", Genetics, 2002, 161:813-824, and Berry, Don et al., "Assessing Probability of Ancestry Using Simple Sequence Repeat Profiles: Applications to Maize Inbred Lines and Soybean Varieties", Genetics, 2003, 165: 331-342.

Particular markers used for these purposes are not limited to the set of markers disclosed herein, but may include any type of marker and marker profile which provides a means of distinguishing varieties. In addition to being used for identification of doubled haploid maize line PHWVZ, a hybrid produced through the use of PHWVZ, and the identification or verification of pedigree for progeny plants produced through the use of PHWVZ, the genetic marker profile is also useful in further breeding and in developing an introgressed trait conversion of PHWVZ.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present.

Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing lines it is preferable if all SSR profiles are performed in the same lab. The SSR analyses reported herein were conducted in-house at Pioneer Hi-Bred. An SSR service is available to the public on a contractual basis by DNA Landmarks in Saint-Jean-sur-Richelieu, Quebec, Canada.

Primers used for the SSRs reported herein are publicly available and may be found in the Maize GDB on the World Wide Web at maizegdb.org (sponsored by the USDA Agricultural Research Service), in Sharopova et al. (Plant Mol. Biol. 48(5-6):463-481), Lee et al. (Plant Mol. Biol. 48(5-6); 453-461), or may be constructed from sequences if reported herein. Primers may be constructed from publicly available sequence information. Some marker information may also be available from DNA Landmarks.

Map information is provided by bin number as reported in the Maize GDB for the IBM 2 and/or IBM 2 Neighbors maps. The bin number digits to the left of decimal point represent the chromosome on which such marker is located, and the digits to the right of the decimal represent the location on such chromosome. A bin number .xx designation indicates that the bin location on that chromosome is not known. Map positions are also available on the Maize GDB for a variety of different mapping populations.

PHWVZ and its plant parts can be identified through a molecular marker profile. An inbred corn plant cell having the SSR genetic marker profile shown in Table 3 is an embodiment of the invention. Such plant cell may be either diploid or haploid.

Also encompassed within the scope of the invention are plants and plant parts substantially benefiting from the use of PHWVZ in their development, such as PHWVZ comprising a introgressed trait through backcross conversion or transformation, and which may be identified by having an SSR molecular marker profile with a high percent identity to PHWVZ, such as at least 80%, 81%, 82%, 83%, 84%, 85%, 86%, 87%, 88%, 89%, 90%, 91%, 92%, 93%, 94%, 95%, 96%, 97%, 98%, 99% or 99.5% identity. Likewise, percent similarity at these percentages may be used to identify hybrid and other non-inbred plants produced by the use of PHWVZ.

An embodiment of this invention is an inbred PHWVZ progeny maize plant or plant part comprising the same homozygous alleles as the plant or plant part of PHWVZ for at least 90% of the SSR loci listed in Table 3. A plant cell comprising the same homozygous alleles as a plant cell of PHWVZ for at least 90% of the SSR loci listed in Table 3 is also an embodiment of this invention. In these specific embodiments, 90% may also be replaced by any integer or partial integer percent of 80% or greater as listed above. One means of producing such a progeny plant, plant part or cell is through the backcrossing and/or transformation methods described herein.

Similarly, an embodiment of this invention is a PHWVZ progeny maize plant or plant part comprising at least one allele per locus that is the same allele as the plant or plant part of PHWVZ for at least 90% of the SSR loci listed in Table 3. This progeny plant may be a hybrid. A progeny or hybrid plant cell wherein at least one allele per locus that is the same allele as the plant cell PHWVZ for at least 90% of the SSR loci listed in Table 3 is also a specific embodiment of this invention. In these specific embodiments, 90% may also be replaced by any integer percent listed above. One means of producing such a progeny or hybrid plant, plant part or cell is through the backcrossing and/or transformation methods described herein.

In addition, the molecular marker profile of PHWVZ also can be used to identify essentially derived varieties and other progeny lines developed from the use of PHWVZ, as well as cells and other plant parts thereof. Progeny plants and plant parts produced using PHWVZ may be identified by having a molecular marker profile of at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PHWVZ, as measured by either percent identity or percent similarity.

Comparing PHWVZ to Other Inbreds

A breeder uses various methods to help determine which plants should be selected from segregating populations and ultimately which inbred lines will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987). Mean trait values may be used to determine whether trait differences are significant. Trait values should preferably be measured on plants grown under the same environmental conditions, and environmental conditions should be appropriate for the traits or traits being evaluated.

Development of Maize Hybrids using PHWVZ

A single cross maize hybrid results from the cross of two inbred lines, each of which has a genotype that complements the genotype of the other. The hybrid progeny of the first generation is designated F1. PHWVZ may be used to produce hybrid maize. One such embodiment is the method of crossing inbred maize line PHWVZ with another maize plant, such as a different maize inbred line, to form a first generation F1 hybrid seed. The first generation F1 hybrid seed, plant and plant part produced by this method is an embodiment of the invention. The first generation F1 seed, plant and plant part will comprise an essentially complete set of the alleles of inbred line PHWVZ. One of ordinary skill in the art can utilize either breeder books or molecular methods to identify a particular F1 hybrid plant produced using inbred line PHWVZ. Further, one of ordinary skill in the art may also produce F1 hybrids with transgenic, male sterile and/or backcross conversions of inbred line PHWVZ.

PHWVZ may be used to produce a single cross hybrid, a double cross hybrid, or a three-way hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. In each case, pericarp tissue from the female parent will be a part of and protect the hybrid seed.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

PHWVZ can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile inbred designated PHWVZ may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's, and the male sterility trait is routinely backcrossed into inbred lines. See Wych, "Production of Hybrid Seed", *Corn and Corn Improvement*, Ch. 9, pp. 565-607, 1998.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 publication no. 329, 308 and PCT application PCT/CA90/00037 published as WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

Introgression of a New Locus or Trait into PHWVZ

PHWVZ represents a new base genetic line into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of PHWVZ

A backcross conversion of PHWVZ occurs when DNA sequences are introduced through backcrossing (Hallauer et al. in Corn and Corn Improvement, Sprague and Dudley, Third Ed. 1998), with PHWVZ utilized as the recurrent parent. Both naturally occurring and transgenic DNA sequences may be introduced through backcrossing techniques. A backcross conversion may produce a plant with a trait or locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding, In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, waxy starch, sterility (nuclear and cytoplasmic), fertility restoration, grain color (white), nutritional enhancements, drought resistance, enhanced nitrogen utilization efficiency, altered nitrogen responsiveness, altered fatty acid profile, increased digestibility, low phytate, industrial enhancements, disease resistance (bacterial, fungal or viral), insect resistance, herbicide resistance and yield enhancements. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into PHWVZ is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration (SSI) system allows for the integration of multiple genes at the converted loci. Further, SSI technologies known to those of skill in the art in the art may result in multiple gene introgressions at a single locus.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. While occasionally additional polynucleotide sequences or genes may be transferred along with the backcross conversion, the backcross conversion line "fits into the same hybrid combination as the recurrent parent inbred line and contributes the effect of the additional gene added through the backcross." Poehlman et al. (1995) *Breeding Field Crop,* 4th Ed., Iowa State University Press, Ames, Iowa., pp. 132-155 and 321-344. It has been proposed that in general there should be at least four backcrosses when it is important that the recovered lines be essentially identical to the recurrent parent except for the characteristic being transferred (Fehr 1987, Principles of Cultivar Development). However, as noted above, the number of backcrosses necessary can be reduced with the use of molecular markers. Other factors, such as a genetically similar donor parent, may also reduce the number of backcrosses necessary.

One process for adding or modifying a trait or locus in maize inbred line PHWVZ comprises crossing PHWVZ plants grown from PHWVZ seed with plants of another maize line that comprise the desired trait or locus, selecting F1 progeny plants that comprise the desired trait or locus to produce selected F1 progeny plants, crossing the selected progeny plants with the PHWVZ plants to produce backcross progeny plants, selecting for backcross progeny plants that have the desired trait or locus and the morphological characteristics of maize inbred line PHWVZ to produce selected backcross progeny plants; and backcrossing to PHWVZ three or more times in succession to produce selected fourth or higher backcross progeny plants that comprise said trait or locus. The modified PHWVZ may be further characterized as having the physiological and morphological characteristics of maize inbred line PHWVZ. Differences in physiological and morphological characteristics can be determined at the 5% significance level when grown in the same environmental conditions and/or may be characterized by percent similarity or identity to PHWVZ as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration.

In addition, the above process and other similar processes described herein may be used to produce F1 hybrid maize seed by adding a step at the end of the process that comprises crossing PHWVZ with the introgressed trait or locus with a different maize plant and harvesting the resultant F1 hybrid maize seed.

Introgression of a New Locus or Trait into PHWVZ through Transformation

Transformation of a PHWVZ cell may also be used in the methods. The type of transformation is not critical to the methods; various methods of transformation are currently available. As newer methods are available to transform host cells they may be directly applied. Accordingly, a wide variety of methods have been developed to insert a DNA sequence into the genome of a host cell to obtain the transcription and/or translation of the sequence. Thus, any method that provides for efficient transformation/transfection may be employed.

Methods for transforming various host cells are disclosed in Klein et al. "Transformation of microbes, plants and animals by particle bombardment", Bio/Technol. New York, N.Y., Nature Publishing Company, March 1992, 10(3):286-291. Techniques for transforming a wide variety of higher plant species are well known and described in the technical, scientific, and patent literature. See, for example, Weising et al., Ann. Rev. Genet. 22:421-477 (1988).

For example, the DNA construct may be introduced directly into the genomic DNA of the plant cell using techniques such as electroporation, PEG-induced transfection, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in Plant Cell, Tissue and Organ Culture, Fundamental Methods. eds. O. L.

Gamborg and G. C. Phillips. Springer-Verlag Berlin Heidelberg New York, 1995. The introduction of DNA constructs using polyethylene glycol precipitation is described in Paszkowski et al., Embo J. 3:2717-2722 (1984). Electroporation techniques are described in Fromm et al., Proc. Natl. Acad. Sci. 82:5824 (1985). Ballistic transformation techniques are described in Klein et al., Nature 327:70-73 (1987). An aerosol transformation method is disclosed in U.S. Pat. No. 7,001,754.

Alternatively, the DNA constructs may be combined with suitable T-DNA flanking regions and introduced into a *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens-meditated* transformation techniques are well described in the scientific literature. See, for example Horsch et al., Science 233:496-498 (1984), and Fraley et al., Proc. Natl. Acad. Sci. 80:4803 (1983). For instance, *Agrobacterium* transformation of maize is described in U.S. Pat. No. 5,981,840. *Agrobacterium* transformation of monocot is found in U.S. Pat. No. 5,591,616. *Agrobacterium* transformation of soybeans is described in U.S. Pat. No. 5,563,055.

Other methods of transformation include (1) *Agrobacterium rhizogenes*-induced transformation (see, e.g., Lichtenstein and Fuller In: Genetic Engineering, vol. 6, P W J Rigby, Ed., London, Academic Press, 1987; and Lichtenstein, C. P., and Draper, J., In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-induced DNA uptake (see, e.g., Freeman et al., Plant Cell Physiol. 25:1353, 1984), (3) the vortexing method (see, e.g., Kindle, Proc. Natl. Acad. Sci., USA 87:1228, (1990).

DNA can also be introduced into plants by direct DNA transfer into pollen as described by Zhou et al., Methods in Enzymology 101:433 (1983); D. Hess, Intern Rev. Cytol. 107:367 (1987); Luo et al., Plant Mol. Biol. Reporter, 6:165 (1988). Expression of polypeptide coding nucleic acids can be obtained by injection of the DNA into reproductive organs of a plant as described by Pena et al., Nature 325:274 (1987). Transformation can also be achieved through electroporation of foreign DNA into sperm cells then microinjecting the transformed sperm cells into isolated embryo sacs as described in U.S. Pat. No. 6,300,543 by Cass et al. DNA can also be injected directly into the cells of immature embryos and the rehydration of desiccated embryos as described by Neuhaus et al., Theor. Appl. Genet. 75:30 (1987); and Benbrook et al., in Proceedings Bio Expo 1986, Butterworth, Stoneham, Mass., pp. 27-54 (1986).

Transformed cells which are derived by any of the above transformation techniques can be cultured to regenerate a whole plant which possesses the transformed genotype. For transformation and regeneration of maize see, Gordon-Kamm et al., The Plant Cell 2:603-618 (1990).

Any DNA sequences, whether from a different species or from the same species, which are inserted into the genome using transformation are referred to herein collectively as "transgenes". In some embodiments of the invention, a transformed variant of PHWVZ may contain at least one transgene but could contain at least 1, 2, 3, 4, 5, 6, 7, 8, 9, or 10. Over the last fifteen to twenty years several methods for producing transgenic plants have been developed, and the present invention also relates to transformed versions of the claimed doubled haploid maize line PHWVZ as well as hybrid combinations thereof.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular maize plant using transformation techniques, could be moved into the genome of another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953, which are herein incorporated by reference.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993).

Wang et al. discuss "Large Scale Identification, Mapping and Genotyping of Single-Nucleotide Polymorphisms in the Human Genome", Science, 280:1077-1082, 1998, and similar capabilities are available for the corn genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of maize the expression of genes can be altered to enhance disease resistance, insect resistance, herbicide resistance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244: 230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) *EMBO J.* 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11 (6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: 5,188,960; 5,689, 052; 5,880,275; WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, J. Biol. Chem. 269: 9 (1994) (expression cloning yields DNA coding for insect diuretic hormone receptor); Pratt et al., Biochem. Biophys. Res. Comm. 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene, U.S. application Ser. Nos. 10/389,432,10/692,367, and U.S. Pat. No. 6,563,020.

(G) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(H) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes et al., Plant Sci. 89:43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2:367 (1992).

(N) A developmental-arrestive protein produced in nature by a plant. For example, Logemann et al., Bio/Technology 10:305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(P) Antifungal genes (Cornelissen and Melchers, P I. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO 03/000863 and U.S. application Ser. No. 10/178,213.

(T) Genes conferring resistance to nematodes. See WO 03/033651 and Urwin et. al., Planta 204:472-479 (1998), Williamson (1999) Curr Opin Plant Bio. 2(4):327-31.

(U) Genes such as rcg1 conferring resistance to Anthracnose stalk rot, which is caused by the fungus *Colletotrichum graminiola*. See M. Jung et al., Generation-means analysis and quantitative trait locus mapping of Anthracnose Stalk Rot genes in Maize, Theor. Appl. Genet. (1994) 89:413-418 which is incorporated by reference for this purpose, as well as U.S. Patent Application 60/675,664, which is also incorporated by reference for this purpose.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclosheones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. 01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., Bio/Technology 7:61 (1989), describe the production of transgenic plants that express chimeric bargenes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cyclosheones, such as sethoxydim and haloxyfop, are the Acc1-S1, Acc1-S2 and Acc1-S3 genes described by Marshall et al., Theor. Appl. Genet. 83: 435 (1992).

(C) A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include:

a gene encoding a chimeric protein of rat cytochrome P4507A1 and yeast NADPH-cytochrome P450 oxidoreductase (Shiota et al. (1994) Plant Physiol. 106(1):17-23), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that confer or contribute to an altered grain characteristic, Such as:

(A) Altered fatty acids, for example, by
  (1) Down-regulation of stearoyl-ACP desaturase to increase stearic acid content of the plant. See Knultzon et al., Proc. Natl. Acad. Sci. USA 89:2624 (1992) and WO 99/64579 (Genes for Desaturases to Alter Lipid Profiles in Corn),
  (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245),
  (3) Altering conjugated linolenic or linoleic acid content, such as in WO 01/12800,
  (4) Altering LEC1, AGP, Dekl, Superall, miups, various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO 02/057439, WO 03/011015 and Rivera-Madrid, R. et. al. Proc. Natl. Acad. Sci. 92:5620-5624 (1995).

(B) Altered phosphorus content, for example, by the
  (1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene.
  (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., Maydica 35: 383 (1990) and/or by altering inositol kinase activity as in WO 02/059324, US 2003/0009011, WO 03/027243, US 2003/0079247, WO 99/05298, U.S. Pat. No. 6,197,561, U.S. Pat. No. 6,291,224, U.S. Pat. No. 6,391,348, WO 2002/059324, US2003/0079247, WO 98/45448, WO 99/55882, WO 01/04147.

(C) Altered carbohydrates effected, for example, by altering a gene for an enzyme that affects the branching pattern of starch or a gene altering thioredoxin such as NTR and/or TRX (see U.S. Pat. No. 6,531,648 which is incorporated by reference for this purpose) and/or a gamma zein knock out or mutant such as cs27 or TUSC27 or en27 (See U.S. Pat. No. 6,858,778 and US 2005/0160488, US 2005/0204418; which are incorporated by reference for this purpose). See Shiroza et al., J. Bacteriol. 170:810 (1988) (nucleotide sequence of *Streptococcus mutans* fructosyltransferase gene), Steinmetz et al., Mol. Gen. Genet. 200:220 (1985) (nucleotide sequence of *Bacillus subtilis* levansucrase gene), Pen et al., Bio/Technology 10:292 (1992) (production of transgenic plants that express *Bacillus licheniformis* alpha-amylase), Elliot et al., Plant Molec. Biol. 21:515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102:1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US 2003/0163838, US 2003/0150014, US 2004/0068767, U.S. Pat. No. 6,803,498, WO 01/79516, and WO 00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. Nos. 10/817,483 and 09/545,334 where cytokinin expression is modified resulting in plants with increased stress tolerance, such as drought tolerance, and/or increased yield. Also see WO 0202776, WO 2003/052063, JP2002281975, U.S. Pat. No. 6,084,153, WO 01/64898, U.S. Pat. No. 6,177,275, and U.S. Pat. No. 6,107,547 (enhancement of nitrogen utilization and altered nitrogen responsiveness). For ethylene alteration, see US 2004/0128719, US 2003/0166197 and WO 2000/32761. For plant transcription factors or transcriptional regulators of abiotic stress, see e.g. US 2004/0098764 or US 2004/0078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FR1), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Using PHWVZ to Develop Other Maize Inbreds

Doubled haploid lines such as PHWVZ provide a source of breeding material that may be used to develop new maize inbred lines. Plant breeding techniques known in the art and used in a maize plant breeding program include, but are not limited to, recurrent selection, mass selection, bulk selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits but genotypic analysis may also be used.

Using PHWVZ in a Breeding Program

This invention is directed to methods for producing a maize plant by crossing a first parent maize plant with a second parent maize plant wherein either the first or second parent maize plant is an inbred maize plant of the line PHWVZ. The other parent may be any other maize plant, such as another inbred line or a plant that is part of a synthetic or natural population. Any such methods using the double haploid maize line PHWVZ are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can also be found in one of several reference books (e.g., Allard, Principles of Plant Breeding, 1960; Simmonds, Principles of Crop Improvement, 1979; Fehr, "Breeding Methods for Cultivar Development", Production and Uses, $2^{nd}$ ed., Wilcox editor, 1987 the disclosure of which is incorporated herein by reference).

Pedigree Breeding

Pedigree breeding starts with the crossing of two genotypes, such as PHWVZ and one other elite inbred line having one or more desirable characteristics that is lacking or which complements PHWVZ. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify PHWVZ and a hybrid that is made using the modified PHWVZ. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection.

Therefore, an embodiment of this invention is a method of making a backcross conversion of double haploid line PHWVZ, comprising the steps of crossing a plant of double haploid line PHWVZ with a donor plant comprising a mutant gene or transgene conferring a desired trait, selecting an F1 progeny plant comprising the mutant gene or transgene conferring the desired trait, and backcrossing the selected F1 progeny plant to a plant of maize inbred line PHWVZ. This method may further comprise the step of obtaining a molecular marker profile of maize inbred line PHWVZ and using the molecular marker profile to select for a progeny plant with the desired trait and the molecular marker profile of PHWVZ. In the same manner, this method may be used to produce an F1 hybrid seed by adding a final step of crossing the desired trait conversion of maize inbred line PHWVZ with a different maize plant to make F1 hybrid maize seed comprising a mutant gene or transgene conferring the desired trait.

Recurrent Selection and Mass Selection

Recurrent selection is a method used in a plant breeding program to improve a population of plants. PHWVZ is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation Breeding

Mutation breeding is one of many methods that could be used to introduce new traits into PHWVZ. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993 Macmillan Publishing Company, the disclosure of which is incorporated herein by reference. In addition, mutations created in other lines may be used to produce a backcross conversion of PHWVZ that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing PHWVZ.

Isozyme Electrophoresis and RFLPs as discussed in Lee, M., "Inbred Lines of Maize and Their Molecular Markers," The Maize Handbook, (Springer-Verlag, New York, Inc. 1994, at 423-432), have been widely used to determine genetic composition. Isozyme Electrophoresis has a relatively low number of available markers and a low number of allelic variants among maize inbreds. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (Zea mays L.): comparisons with data from RFLPs and pedigree", Theoretical and Applied Genetics (1997) vol. 95 at 163-173 and by Pejic et al., "Comparative analysis of genetic similarity among maize inbreds detected by RFLPs, RAPDs, SSRs, and AFLPs," Theoretical and Applied Genetics (1998) at 1248-1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of inbreds in the breeding program. For example, an F1 hybrid for which PHWVZ is a parent can be used to produce double haploid plants. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, *Am. Nat.* 93:381-382; Sharkar and Coe, 1966, *Genetics* 54:453-464) RWS (see world wide web site www.uni-hohenheim.de%7Eipspwww/350b/indexe.html#Project3), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424). The disclosures of which are incorporated herein by reference.

Methods for obtaining haploid plants are also disclosed in Kobayashi, M. et al., Journ. of Heredity 71(1):9-14,1980, Pollacsek, M., Agronomie (Paris) 12(3):247-251,1992; Cho-Un-Haing et al., Journ. of Plant Biol., 1996, 39(3):185-188; Verdoodt, L., et al., Feb. 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, Maize Genet. Coop. Newsletter 73:53-54; Coe, R. H., 1959, Am. Nat. 93:381-382; Deimling, S. et al., 1997, Vortr. Pflanzenzuchtg 38:203-204; Kato, A., 1999, J. Hered. 90:276-280; Lashermes, P. et al., 1988, Theor. Appl. Genet. 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M.A., 1978, Indian J. Genet Plant Breed 38:452-457; Chalyk S. T., 1994, Euphytica 79:13-18; Chase, S. S., 1952, Agron. J. 44:263-267; Coe, E. H., 1959, Am. Nat. 93:381-382; Coe, E. H., and Sarkar, K. R., 1964 J. Hered. 55:231-233; Greenblatt, I. M. and Bock, M., 1967, J. Hered. 58:9-13; Kato, A., 1990, Maize Genet. Coop. Newsletter 65:109-110; Kato, A., 1997, Sex. Plant Reprod. 10:96-100; Nanda, D. K. and Chase, S. S., 1966, Crop Sci. 6:213-215; Sarkar, K. R. and Coe, E. H., 1966, Genetics 54:453-464; Sarkar, K. R. and Coe, E. H., 1971, Crop Sci. 11:543-544; Sarkar, K. R. and Sachan J. K. S., 1972, Indian J. Agric. Sci. 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000,119(4):289-298; U.S. Pat. No. 5,639,951 and U.S. patent application Ser. No. 10/121,200, the disclosures of which are incorporated herein by reference.

Thus, an embodiment of this invention is a process for making a substantially homozygous PHWVZ progeny plant by producing or obtaining a seed from the cross of PHWVZ and another maize plant and applying double haploid methods to the F1 seed or F1 plant or to any successive filial generation. Such methods decrease the number of generations required to produce an inbred with similar genetics or characteristics to PHWVZ. See Bernardo, R. and Kahler, A. L., Theor. Appl. Genet. 102:986-992, 2001.

In particular, a process of making seed retaining the molecular marker profile of maize inbred line PHWVZ is contemplated, such process comprising obtaining or producing F1 hybrid seed for which maize inbred line PHWVZ is a parent, inducing doubled haploids to create progeny without the occurrence of meiotic segregation, obtaining the molecular marker profile of maize inbred line PHWVZ, and selecting progeny that retain the molecular marker profile of PHWVZ.

Use of PHWVZ in Tissue Culture

This invention is also directed to the use of PHWVZ in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widholm, Planta (1985) 165: 322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. 2002/0062506A1 and European Patent Application, publication EP0160,390, each of which are incorporated herein by reference for this purpose. Maize tissue culture procedures are also described in Green and Rhodes, "Plant Regeneration in Tissue Culture of Maize," Maize for Biological Research "Plant Regeneration in Tissue Cultures of Maize" (1N Maize for Biological Research, 1982, pp. 367-372) and in Duncan, et al., "The Production of Callus Capable of Plant Regeneration from Immature Embryos of Numerous *Zea Mays* Genotypes," 165 Planta 322-332 (1985). Thus, another aspect of this invention is to provide cells which upon growth and differentiation produce maize plants having the genotype and/or physiological and morphological characteristics of inbred line PHWVZ.

Progeny Plants

All plants produced by the use of the methods described herein and that retain the unique genetic or trait combinations of PHWVZ are within the scope of the invention. Progeny of the breeding methods described herein may be characterized in any number of ways, such as by traits retained in the progeny, pedigree and/or molecular markers. Combinations of these methods of characterization may be used.

Breeder's of ordinary skill in the art have developed the concept of an "essentially derived variety", which is defined in 7 U.S.C. §2104(a)(3) of the Plant Variety Protection Act and is hereby incorporated by reference. Varieties and plants that are essentially derived from PHWVZ are within the scope of the invention.

Pedigree is a method used by breeders of ordinary skill in the art to describe the varieties. Varieties that are more closely related by pedigree are likely to share common genotypes and combinations of phenotypic characteristics. All breeders of ordinary skill in the art maintain pedigree records of their breeding programs. These pedigree records contain a detailed description of the breeding process, including a listing of all parental lines used in the breeding process and information on how such line was used. One embodiment of this invention is progeny plants and parts thereof with at least one ancestor that is PHWVZ, and more specifically, where the pedigree of the progeny includes 1, 2, 3, 4, and/or 5 or less breeding crosses to a maize plant other than PHWVZ or a plant that has PHWVZ as a parent or other progenitor. A breeder of ordinary skill in the art would know if PHWVZ were used in the development of a progeny line, and would also know how many crosses to a line other than PHWVZ or line with PHWVZ as a parent or other progenitor were made in the development of any progeny line.

Molecular markers also provide a means by which those of ordinary skill in the art characterize the similarity or differences of two lines. Using the breeding methods described herein, one can develop individual plants, plant cells, and populations of plants that retain at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PHWVZ, as measured by either percent identity or percent similarity. On average 50% of the starting germplasm would be expected to be passed to the progeny line after one cross to another line, 25% after another cross to a different line, and so on. With backcrossing, the expected contribution of PHWVZ after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

A breeder will commonly work to combine a specific trait of an undeveloped variety of the species, such as a high level of resistance to a particular disease, with one or more of the elite agronomic characteristics (yield, maturity, plant size, lodging resistance, etc.) needed for use as a commercial variety. This combination, once developed, provides a valuable source of new germplasm for further breeding. For example, it may take 10-15 years and significant effort to produce such a combination, yet progeny may be developed that retain this combination in as little as 2-5 years and with much less effort.

Specific Embodiments

Specific methods and products produced using double haploid line PHWVZ in plant breeding are discussed in the following sections. The methods outlined are described in detail by way of illustration and example for purposes of clarity and understanding. However, it will be obvious that certain changes and modifications may be practiced within the scope of the invention.

One method for producing a line derived from inbred line PHWVZ is as follows. One of ordinary skill in the art would produce or obtain a seed from the cross between inbred line PHWVZ and another variety of maize, such as an elite inbred variety. The F1 seed derived from this cross would be grown to form a homogeneous population. The F1 seed would contain essentially all of the alleles from variety PHWVZ and essentially all of the alleles from the other maize variety. The F1 nuclear genome would be made-up of 50% variety PHWVZ and 50% of the other elite variety. The F1 seed would be grown and allowed to self, thereby forming F2 seed. On average the F2 seed would have derived 50% of its alleles from variety PHWVZ and 50% from the other maize variety, but many individual plants from the population would have a greater percentage of their alleles derived from PHWVZ (Wang J. and R. Bernardo, 2000, Crop Sci. 40:659-665 and Bernardo, R. and A. L. Kahler, 2001, Theor. Appl. Genet. 102:986-992). The molecular markers of PHWVZ could be used to select and retain those lines with high similarity to PHWVZ. The F2 seed would be grown and selection of plants would be made based on visual observation, markers and/or measurement of traits. The traits used for selection may be any PHWVZ trait described in this specification, including the inbred per se maize PHWVZ traits described herein under the detailed description of inbred PHWVZ. Such traits may also be the good general or specific combining ability of PHWVZ, including its ability to produce hybrids with the approximate maturity and/or hybrid combination traits described herein under the detailed description of inbred PHWVZ. The PHWVZ progeny plants that exhibit one or more of the desired PHWVZ traits, such as those listed herein, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable PHWVZ traits listed herein. The process of growing and selection would be repeated any number of times until a PHWVZ progeny inbred plant is obtained. The PHWVZ progeny inbred plant would contain desirable traits derived from inbred plant PHWVZ, some of which may not have been expressed by the other maize variety to which inbred line PHWVZ was crossed and some of which may have been expressed by both maize varieties but now would be at a level equal to or greater than the level expressed in inbred variety PHWVZ. However, in each case the resulting progeny line would benefit from the efforts of the inventor(s), and would not have existed but for the inventor(s) work in creating PHWVZ. The PHWVZ progeny inbred plants would have, on average, 50% of their nuclear genes derived from inbred line PHWVZ, but many individual plants from the population would have a greater percentage of their alleles derived from PHWVZ. This breeding cycle, of crossing and selfing, and optional selection, may be repeated to produce another population of PHWVZ progeny maize plants with, on average, 25% of their nuclear genes derived from inbred line PHWVZ, but, again, many individual plants from the population would have a greater percentage of their alleles derived from PHWVZ. This process can be repeated for a third, fourth, fifth, sixth, seventh or more breeding cycles. Another embodiment of the invention is a PHWVZ progeny plant that has received the desirable PHWVZ traits listed herein through the use of PHWVZ, which traits were not exhibited by other plants used in the breeding process.

Therefore, an embodiment of this invention is a PHWVZ progeny maize plant, wherein at least one ancestor of said PHWVZ progeny maize plant is the maize plant or plant part of PHWVZ, and wherein the pedigree of said PHWVZ progeny maize plant is within two breeding crosses of PHWVZ or a plant that has PHWVZ as a parent. The progeny plants, parts and plant cells produced from PHWVZ may be further characterized as having a percent marker similarity or identity with PHWVZ as described herein.

The previous example can be modified in numerous ways, for instance selection may or may not occur at every selfing generation, selection may occur before or after the actual self-pollination process occurs, or individual selections may be made by harvesting individual ears, plants, rows or plots at any point during the breeding process described. Double haploid breeding methods may be used at any step in the process. Instead of selfing out of the hybrid produced from the inbred, one could first cross the hybrid to either a parent line or a different inbred, and then self out of that cross.

The population of plants produced at each and any cycle of breeding is also an embodiment of the invention, and on average each such population would predictably consist of plants containing approximately 50% of its genes from double haploid line PHWVZ in the first breeding cycle, 25% of its genes from double haploid line PHWVZ in the second breeding cycle, 12.5% of its genes from inbred line PHWVZ in the third breeding cycle, 6.25% in the fourth breeding cycle, 3.125% in the fifth breeding cycle, and so on. However, in each case the use of PHWVZ provides a substantial benefit. The linkage groups of PHWVZ would be retained in the progeny lines, and since current estimates of the maize genome size is about 50,000-80,000 genes (Xiaowu, Gai et al., Nucleic Acids Research, 2000, Vol. 28, No. 1, 94-96), in addition to non-coding DNA that impacts gene expression, it provides a significant advantage to use PHWVZ as starting material to produce a line that retains desired genetics or traits of PHWVZ.

Therefore, an embodiment of the invention is a process for making a population of PHWVZ progeny inbred maize plants comprising obtaining or producing a first generation progeny maize seed comprising the plant of PHWVZ as a parent, growing said first generation progeny maize seed to produce first generation maize plants and obtaining self or sib pollinated seed from said first generation maize plants, and growing the self or sib pollinated seed to obtain a population of PHWVZ progeny inbred maize plants.

The population of PHWVZ progeny inbred maize plants produced by this method are also embodiments of the invention, and such population as a whole will retain the expected genetic contribution of PHWVZ. An inbred line selected from the population of PHWVZ progeny inbred maize plants produced by this method is an embodiment, and such line may be further characterized by its molecular marker identity or similarity to PHWVZ.

In this manner, the invention also encompasses a process for making a PHWVZ inbred progeny maize plant comprising the steps of obtaining or producing a first generation progeny maize seed wherein a parent of said first generation progeny maize seed is a PHWVZ plant, growing said first generation progeny maize seed to produce a first generation maize plant and obtaining self or sib pollinated seed from said first generation maize plant, and producing successive filial generations to obtain a PHWVZ inbred progeny maize plant. Also an embodiment of this invention is the first breeding cycle inbred PHWVZ maize plant produced by this method.

Crosses to Other Species

The utility of inbred maize line PHWVZ also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with PHWVZ may be the various varieties of grain sorghum, *Sorghum bicolor* (L.) Moench.

DEPOSITS

Applicant has made a deposit of at least 2500 seeds of double haploid maize line PHWVZ with the American Type Culture Collection (ATCC), Manassas, Va. 20110 USA, ATCC Accession No. PTA-11811. The seeds deposited with the ATCC on May 2, 2011 were taken from the deposit maintained by Pioneer Hi-Bred International, Inc., 7250 NW 62$^{nd}$ Avenue, Johnston, Iowa, 50131 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of the Inbred Maize Line PHWVZ will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.). U.S. Plant Variety Protection of Inbred Maize Line PHWVZ has been applied for. Unauthorized seed multiplication prohibited.

TABLE 3

SSR Profile Data for PHWVZ

| Bin | Marker Name | Base Pairs |
|---|---|---|
| 1.00 | umc1041 | 326.73 |
| 1.00 | umc1354 | 309.53 |
| 1.01 | phi427913 | 129.58 |
| 1.01 | umc2215 | 145.01 |
| 1.01 | bnlg1014 | 131.81 |
| 1.01 | umc1071 | 116.85 |
| 1.01 | umc1177 | 107.58 |
| 1.01 | umc1269 | 344.2 |
| 1.02 | umc2225 | 331.61 |
| 1.02 | dupssr2 | 311.07 |
| 1.02 | bnlg1007 | 126.62 |
| 1.02 | bnlg1083 | 221.67 |
| 1.02 | bnlg1127 | 96.28 |
| 1.02 | bnlg1953 | 248.02 |
| 1.02 | bnlg1429 | 190.38 |
| 1.02 | umc1166 | 88.14 |
| 1.03 | phi109275 | 125.91 |
| 1.03 | phi339017 | 149.05 |
| 1.03 | umc1044 | 140.9 |
| 1.03 | umc1701 | 117.73 |
| 1.04 | bnlg2086 | 218.1 |
| 1.04 | umc1144 | 230.27 |

TABLE 3-continued

SSR Profile Data for PHWVZ

| Bin | Marker Name | Base Pairs |
|---|---|---|
| 1.04 | umc1169 | 165.59 |
| 1.05 | umc1244 | 348.27 |
| 1.05 | umc1297 | 159.88 |
| 1.06 | umc1035 | 237.35 |
| 1.06 | bnlg1832 | 215.8 |
| 1.06 | bnlg1615 | 211.56 |
| 1.06 | umc1123 | 307.41 |
| 1.06 | umc1281 | 344.68 |
| 1.07 | bnlg1556 | 201.57 |
| 1.07 | phi002 | 73.52 |
| 1.07 | umc1128 | 227.84 |
| 1.07 | umc1245 | 305.45 |
| 1.08 | dupssr12 | 124.86 |
| 1.08 | phi335539 | 88.48 |
| 1.08 | phi423298 | 133.11 |
| 1.09 | umc1306 | 147.64 |
| 1.09 | bnlg1331 | 120.82 |
| 1.09 | bnlg1720 | 236.6 |
| 1.09 | phi011 | 226.59 |
| 1.09 | umc1298 | 362.5 |
| 1.10 | umc1774 | 149.87 |
| 1.10 | phi308707 | 131.27 |
| 1.11 | umc1630 | 186.49 |
| 1.11 | phi227562 | 319.63 |
| 1.11 | phi265454 | 233.92 |
| 1.11 | phi064 | 93.52 |
| 1.11 | umc1129 | 350.13 |
| 2.00 | phi402893 | 218.14 |
| 2.02 | umc1265 | 311.26 |
| 2.02 | bnlg1017 | 195.31 |
| 2.03 | phi109642 | 147.76 |
| 2.04 | umc1326 | 142 |
| 2.04 | umc1024 | 326.01 |
| 2.04 | umc1026 | 123.73 |
| 2.06 | umc1004 | 162.87 |
| 2.06 | bnlg1036 | 191.02 |
| 2.06 | bnlg1138 | 214.28 |
| 2.06 | bnlg1396 | 133.58 |
| 2.06 | bnlg1831 | 194.26 |
| 2.06 | umc1080 | 248.53 |
| 2.06 | umc1156 | 234.7 |
| 2.07 | phi251315 | 123.96 |
| 2.07 | umc1560 | 136.33 |
| 2.07 | umc1108 | 205.36 |
| 2.08 | dupssr25 | 214.62 |
| 2.08 | phi328189 | 115.38 |
| 2.08 | phi427434 | 130.74 |
| 2.08 | phi435417 | 217.78 |
| 2.08 | umc1049 | 127.63 |
| 2.08 | bnlg1940 | 219.06 |
| 2.08 | bnlg1258 | 245.17 |
| 2.08 | phi090 | 145.4 |
| 2.08 | umc1230 | 310.03 |
| 2.09 | umc1736 | 283.46 |
| 2.09 | bnlg1520 | 285.97 |
| 2.10 | phi101049 | 234.11 |
| 2.10 | umc2214 | 287.62 |
| 3.01 | phi104127 | 169.34 |
| 3.01 | phi404206 | 302.74 |
| 3.02 | phi193225 | 136.72 |
| 3.02 | phi374118 | 225.13 |
| 3.02 | bnlg1647 | 164.13 |
| 3.04 | phi243966 | 211.96 |
| 3.04 | bnlg1019 | 154.98 |
| 3.04 | bnlg1113 | 134.37 |
| 3.04 | bnlg1638 | 142.14 |
| 3.04 | bnlg1452 | 125.38 |
| 3.04 | bnlg1816 | 283.77 |
| 3.04 | phi029 | 157.58 |
| 3.04 | umc1012 | 134.1 |
| 3.04 | umc1025 | 159.51 |
| 3.04 | umc1030 | 240.02 |
| 3.04 | umc1347 | 228.46 |
| 3.05 | bnlg1035 | 100.91 |
| 3.05 | phi053 | 166.65 |
| 3.05 | phi073 | 187.17 |
| 3.05 | umc1102 | 197.15 |
| 3.05 | umc1167 | 341.08 |
| 3.05 | umc1174 | 312.42 |
| 3.05 | umc1300 | 164.67 |
| 3.05 | umc1307 | 134.41 |
| 3.06 | bnlg1160 | 210.41 |
| 3.06 | bnlg1951 | 120.9 |
| 3.06 | bnlg2241 | 186.45 |
| 3.06 | umc1027 | 201.2 |
| 3.06 | umc1266 | 239.62 |
| 3.06 | umc1311 | 211.83 |
| 3.07 | umc1135 | 224.15 |
| 3.07 | umc1148 | 312.09 |
| 3.07 | umc1286 | 233.99 |
| 3.08 | umc1273 | 205.85 |
| 3.09 | bnlg1496 | 196.23 |
| 3.09 | umc1052 | 155.1 |
| 4.01 | phi213984 | 284.1 |
| 4.01 | phi295450 | 185.14 |
| 4.03 | adh2 | 117.57 |
| 4.04 | mmc0471 | 222.03 |
| 4.05 | bnlg1217 | 212.31 |
| 4.05 | umc1175 | 282.11 |
| 4.05 | bnlg1937 | 227.57 |
| 4.05 | bnlg1265 | 223.86 |
| 4.05 | umc1142 | 155.35 |
| 4.05 | umc1303 | 127.22 |
| 4.05 | umc1346 | 93.6 |
| 4.06 | bnlg252 | 165.74 |
| 4.06 | mmc0371 | 275.06 |
| 4.06 | umc1299 | 142.31 |
| 4.07 | bnlg1927 | 199.65 |
| 4.07 | dupssr34 | 307.6 |
| 4.07 | umc2038 | 122.13 |
| 4.07 | umc1194 | 167.03 |
| 4.08 | dupssr28 | 128.32 |
| 4.08 | phi066 | 159.94 |
| 4.08 | umc1051 | 125.59 |
| 4.08 | umc1086 | 100.11 |
| 4.08 | umc1132 | 132.14 |
| 4.08 | umc1371 | 124.64 |
| 4.08 | umc2188 | 161.9 |
| 4.09 | phi314704 | 136.18 |
| 4.09 | bnlg1565 | 208.42 |
| 4.09 | umc1101 | 137.29 |
| 4.09 | umc1173 | 160.85 |
| 4.09 | umc1284 | 144.36 |
| 4.09 | umc1328 | 161.22 |
| 4.11 | bnlg1890 | 200.79 |
| 5.00 | umc1097 | 109.54 |
| 5.00 | umc1240 | 207.4 |
| 5.01 | phi024 | 367.38 |
| 5.01 | umc1365 | 115.08 |
| 5.02 | phi396160 | 298.12 |
| 5.03 | phi109188 | 161.21 |
| 5.03 | umc1048 | 137.43 |
| 5.03 | umc1315 | 159.03 |
| 5.03 | umc1355 | 357.91 |
| 5.04 | phi330507 | 140.29 |
| 5.04 | phi331888 | 134.05 |
| 5.04 | bnlg1208 | 134.76 |
| 5.04 | bnlg2323 | 203.9 |
| 5.04 | umc1060 | 246.81 |
| 5.04 | umc1092 | 134.59 |
| 5.04 | umc1221 | 162.45 |
| 5.04 | umc1224 | 132.84 |
| 5.04 | umc1332 | 232.25 |
| 5.05 | umc2386 | 124.45 |
| 5.05 | phi333597 | 216.2 |
| 5.07 | bnlg1118 | 82.55 |
| 5.07 | umc1375 | 143.29 |
| 5.08 | umc1225 | 110.23 |
| 5.09 | bnlg386 | 133.05 |
| 5.09 | umc1153 | 105.17 |

TABLE 3-continued

SSR Profile Data for PHWVZ

| Bin | Marker Name | Base Pairs |
|---|---|---|
| 6.00 | umc1143 | 236.08 |
| 6.01 | phi423796 | 128.14 |
| 6.01 | bnlg1422 | 215.98 |
| 6.01 | phi077 | 124.81 |
| 6.01 | umc1133 | 228.91 |
| 6.01 | umc1186 | 268.91 |
| 6.01 | umc1195 | 138.32 |
| 6.01 | umc1229 | 215.93 |
| 6.02 | umc1083 | 345.35 |
| 6.03 | phi389203 | 309.3 |
| 6.03 | umc1002 | 123.58 |
| 6.04 | umc2317 | 128.74 |
| 6.04 | phi452693 | 122.33 |
| 6.04 | umc1014 | 327.14 |
| 6.05 | phi445613 | 100.17 |
| 6.05 | umc1413 | 297.98 |
| 6.05 | umc1114 | 210.79 |
| 6.05 | umc1187 | 134.21 |
| 6.05 | umc1314 | 342.07 |
| 6.07 | phi299852 | 107.94 |
| 6.07 | phi364545 | 131.27 |
| 6.07 | bnlg1740 | 194.45 |
| 6.07 | phi070 | 77.87 |
| 6.07 | umc1248 | 100.18 |
| 6.07 | umc1350 | 122.93 |
| 7.00 | bnlg2132 | 200.43 |
| 7.00 | umc1241 | 120.96 |
| 7.01 | umc1159 | 234.07 |
| 7.01 | bnlg1292 | 138.63 |
| 7.01 | phi057 | 416.74 |
| 7.01 | umc1066 | 341.92 |
| 7.02 | dupssr9 | 116.37 |
| 7.02 | umc2327 | 136.58 |
| 7.02 | bnlg1094 | 157.41 |
| 7.02 | phi034 | 119.78 |
| 7.02 | umc1016 | 349.88 |
| 7.02 | umc1036 | 299.54 |
| 7.02 | umc1068 | 340.98 |
| 7.02 | umc1138 | 255.72 |
| 7.02 | umc1339 | 133.23 |
| 7.03 | bnlg155 | 262.83 |
| 7.03 | bnlg1070 | 145.57 |
| 7.03 | bnlg2271 | 233.8 |
| 7.03 | umc1001 | 144.97 |
| 7.03 | umc1112 | 248.07 |
| 7.03 | umc1134 | 320.87 |
| 7.03 | umc1275 | 313.78 |
| 7.03 | umc1301 | 334.88 |
| 7.03 | umc1324 | 211.83 |
| 7.04 | phi328175 | 98.28 |
| 7.04 | umc1342 | 230.53 |
| 7.04 | umc1799 | 104.18 |
| 7.05 | phi260485 | 284.9 |
| 7.05 | phi082 | 222.93 |
| 7.05 | phi051 | 138.27 |
| 7.05 | phi069 | 195.23 |
| 7.05 | umc1154 | 261.17 |
| 7.06 | phi116 | 164.79 |
| 8.00 | phi420701 | 297.88 |
| 8.01 | umc1075 | 243.97 |
| 8.01 | umc1139 | 305.91 |
| 8.02 | umc1304 | 251.38 |
| 8.03 | phi100175 | 144.97 |
| 8.03 | bnlg1863 | 213.31 |
| 8.03 | phi115 | 302.17 |
| 8.03 | phi121 | 93.35 |
| 8.03 | umc1157 | 218.57 |
| 8.03 | umc1377 | 216.16 |
| 8.03 | umc1457 | 341.2 |
| 8.04 | bnlg2046 | 306.04 |
| 8.04 | umc1172 | 331.07 |
| 8.04 | umc1343 | 317.37 |
| 8.05 | umc1130 | 256.89 |
| 8.05 | umc1263 | 348.44 |
| 8.05 | umc1316 | 237.19 |
| 8.05 | umc1340 | 212.19 |
| 8.06 | umc1149 | 226.96 |
| 8.06 | umc1161 | 257.96 |
| 8.07 | bnlg1065 | 226.72 |
| 8.07 | bnlg1828 | 158.74 |
| 8.08 | bnlg1056 | 94.48 |
| 8.08 | phi015 | 99.64 |
| 8.09 | dupssr14 | 319.6 |
| 8.09 | phi233376 | 135.56 |
| 8.09 | umc1663 | 201.58 |
| 9.01 | umc1867 | 232.46 |
| 9.01 | bnlg1810 | 197.38 |
| 9.01 | bnlg2122 | 237.02 |
| 9.02 | umc1131 | 362.36 |
| 9.02 | umc1170 | 240.87 |
| 9.03 | bnlg127 | 222.32 |
| 9.03 | gl15 | 157.33 |
| 9.03 | phi022 | 258.33 |
| 9.03 | umc1191 | 251.13 |
| 9.04 | bnlg1012 | 161.49 |
| 9.04 | umc1107 | 210.65 |
| 9.05 | mmp179 | 161.53 |
| 9.05 | phi108411 | 126.45 |
| 9.05 | umc1357 | 251.12 |
| 9.07 | bnlg1375 | 117.68 |
| 9.07 | dupssr29 | 97.71 |
| 9.07 | umc1104 | 216.61 |
| 9.07 | umc1277 | 236.55 |
| 10.00 | phi041 | 202.11 |
| 10.00 | umc1293 | 160.87 |
| 10.01 | umc1291 | 341.59 |
| 10.01 | umc1318 | 216.3 |
| 10.02 | umc1337 | 313.61 |
| 10.02 | phi96342 | 249.64 |
| 10.02 | phi059 | 152.93 |
| 10.03 | bnlg1079 | 172.32 |
| 10.03 | bnlg1655 | 126.43 |
| 10.03 | phi050 | 83.31 |
| 10.03 | umc1312 | 315.63 |
| 10.03 | umc1336 | 310.05 |
| 10.03 | umc1345 | 166.48 |
| 10.03 | umc1367 | 327.29 |
| 10.04 | phi301654 | 128.01 |
| 10.04 | umc1246 | 230.45 |
| 10.04 | umc1272 | 206.55 |
| 10.04 | umc1280 | 432.72 |
| 10.04 | umc1330 | 340.3 |
| 10.05 | phi323152 | 134.51 |
| 10.05 | bnlg1074 | 183.9 |
| 10.06 | umc1045 | 173.21 |
| 10.07 | bnlg1839 | 205.98 |
| 10.07 | umc1038 | 261.08 |
| 10.07 | umc1084 | 241.16 |
| 10.07 | umc1176 | 348.57 |
| 10.07 | umc1344 | 210.48 |
| 10.7 | bnlg1185 | 189.14 |

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A seed of maize line designated PHWVZ, representative seed of said line having been deposited under ATCC Accession number PTA-11811.

2. A maize plant, or a part thereof, produced by growing the seed of claim 1.

3. Pollen of the plant of claim 2.

4. An ovule or ovules of the plant of claim 2.

5. A maize cell from the maize plant of claim 2.

6. A method of introducing a transgene into a maize cell comprising: transforming the maize cell of claim 5 with the transgene.

7. Protoplast produced from the maize plant cell of claim 5.

8. A maize plant cell comprising 95% of the alleles of double haploid line PHWVZ at the molecular marker loci listed in Table 3, representative seed of said line having been deposited under ATCC Accession number PTA-11811.

9. The maize plant cell of claim 8 comprising 98% of said alleles.

10. The maize plant cell of claim 8 comprising 99% of said alleles.

11. The maize plant cell of claim 8 comprising 100% of said alleles.

12. A method of introducing a transgene into a maize plant cell comprising: transforming the maize plant cell of claim 8 with the transgene.

13. A process for producing an F1 hybrid maize seed, said process comprising crossing the plant of claim 2 with a different maize plant and harvesting F1 hybrid maize seed.

14. The process of claim 13, further comprising growing the F1 hybrid maize seed to produce a hybrid maize plant.

15. The process of claim 13, further comprising culturing a cell from the F1 hybrid maize seed.

16. A plant according to claim 2, wherein said plant is modified by the addition of at least one mutant or transgenic gene that confers a characteristic selected from the group consisting of male sterility, herbicide resistance, increased transformability, increased culturability, a colored marker, an inducible marker, site-specific recombination, disease resistance, insect resistance, altered phosphorus, altered antioxidants, altered fatty acids, altered essential amino acids, altered carbohydrates and abiotic stress tolerance.

17. The maize plant of claim 16, wherein said site-specific recombination is conferred by a member of the group consisting of flp/frt, cre/lox, Gin, Pin, and R/RS.

18. A process of producing an F1 cell comprising crossing a double haploid maize line PHWVZ plant grown from PHWVZ seed, representative seed of which has been deposited under ATCC Accession number PTA-11811, with another maize line to produce an F1 cell.

19. The F1 cell produced by the process of claim 18.

* * * * *